United States Patent [19]

Revici

[11] Patent Number: 4,624,851

[45] Date of Patent: Nov. 25, 1986

[54] TREATMENT OF SYMPTOMS OF NEOPLASTIC DISEASES

[75] Inventor: Emanuel Revici, New York, N.Y.

[73] Assignee: Elena Avram, New York, N.Y.

[21] Appl. No.: 714,359

[22] Filed: Mar. 22, 1985

Related U.S. Application Data

[63] Continuation of Ser. No. 487,901, Apr. 22, 1983, abandoned.

[51] Int. Cl.[4] .................... A61K 33/42; A61K 33/16; A61K 31/19; A61K 31/20

[52] U.S. Cl. .................................... 424/128; 424/151; 514/557; 514/560; 514/508; 514/574

[58] Field of Search ................ 424/128, 151; 514/557, 514/560, 574, 568

[56] References Cited

PUBLICATIONS

Hirschberg, Cancer Research, Part 2, vol. 23, No. 5, Jun. 1963, p. 747.

Primary Examiner—Jerome D. Goldberg
Attorney, Agent, or Firm—Pennie & Edmonds

[57] ABSTRACT

The method of treating neoplasms in lower animals and humans by administering thereto fluorine containing acids or their non-toxic salts or esters.

11 Claims, No Drawings

TREATMENT OF SYMPTOMS OF NEOPLASTIC DISEASES

This is a continuation of application Ser. No. 487,901, filed Apr. 22, 1983, now abandoned.

The present invention is concerned with a method of treating the symptoms of neoplastic diseases and more particularly, the use of fluorine containing acids for alleviating symptoms of neoplastic diseases without treating the disease itself.

The fluorine containing acid that can be administered to the body for alleviating symptoms of neoplastic conditions without treating the disease itself include perfluorobutyric acid, perfluoroglutamic acid, perfluorooctanoic acid, perfluoropropionic acid, perfluorosuccinic acid, hexafluorophosphoric acid, fluoroacetic acid, fluorobenzoic acid, fluoromethylbenzoic acid, and fluorosulfuric acid. The above fluoroacids are given as representative and the invention does not exclude the use of other fluorine containing acids. The non-toxic salts of esters of the fluorine containing acids can also be employed. The ammonia ($NH_3$) salts are at present perferred. The organic fluorine containing acid can contain various amounts of fluorine atoms, however, a significant decrease in activity appears to result when these acids contain 20 or more fluorine atoms. It is thus advantageous to employ fluorine containing organic acids having less fluorine atoms. Best results to date are obtained with perfluorooctanoic acid and hexafluorophosphoric acid, particularly their ammonium salts. The fluorine containing acids can also be used in admixtures with each other.

The fluorine containing acids can be water soluble or water insoluble and either can be used directly in solution, e.g., water or alcohol, or in conventional therapeutic emulsion form.

The required dosage will, of course, depend upon the particular fluorine containing acid being employed as well as the extent of the neoplasm in the patient. Generally, especially with hexafluorophosphoric acid, from about 100 mcg. to 50 milligrams is sufficient. The appearance of a slight dizziness is a factor limiting the use of progressively increasing dosages. The treatment can be continued at various intervals, preferably daily, until maximum effect is obtained. Administration can be orally or by injection.

No claim is made that the use of fluorine containing acids will cure neoplasms but subjective improvements result in various symptoms of neoplastic conditions, such as cancers, sarcomas, lymphomas, leukemias as well as in benign tumors. The use of the fluorine containing acids is noted to reduce pain and alleviate other known symptoms of neoplastic conditions. The invention is useful for treating symptoms of neoplasms in the lower animals as well as in humans.

I claim:

1. A method for treating at least some of the symptoms of cancer in a human or lower animal subject without treating the cancer which comprises administering to said subject an effective amount of perfluorobutyric acid, perfluorooctanoic acid, perfluoropropionic acid, perfluorosuccinic acid, hexafluorophosphoric acid, fluorobenzoic acid, fluoromethylbenzoic acid, or fluorosulfuric acid, or pharmaceutically acceptable salt thereof.

2. The method of claim 1 wherein the amount of said acid or salt is between about 100 mcg and 50 mg.

3. The method of claim 1 wherein the amount of said acid or salt is administered orally or by injection.

4. The method of claim 1 wherein the amount of said acid or salt is administered daily.

5. The method of claim 1 wherein the amount of said salt is an ammonium salt.

6. The method of claim 1 wherein the amount of said acid or salt is in a water or alcohol solution, or in the form of an emulsion.

7. A method for obtaining subjective improvements in the treatment of symptoms of cancer in a human or lower animal subject without treating the cancer which comprises administering to said subject between about 100 mcg to 50 mg daily of a perfluorobutyric acid, perfluorooctanoic acid, perfluoropropionic acid, perfluorosuccinic acid, hexafluorophosphoric acid, fluorobenzoic acid, fluoromethylbenzoic acid, fluorosulfuric acid, or pharmaceutically acceptable salt thereof.

8. The method of claim 7 wherein the amount of said acid or salt is administered orally or by injection.

9. The method of claim 7 wherein the amount of said salt is an ammonium salt.

10. The method of claim 7 wherein the amount of said acid or salt is in a water or alcohol solution, or in the form of an emulsion.

11. A method for alleviating some of the sumptoms of cancer in a human or lower animal subject without treating the cancer which comprises orally administering to said subject a water solution of between 100 mcg to 50 mg of perfluorobutyric acid, perfluorooctanoic acid, perfluoropropionic acid, perfluorosuccinic acid, hexafluorophosphoric acid, fluorobenzoic acid, fluoromethylbenzoic acid, fluorosulfuric acid or pharmaceutically acceptable ammonium salt thereof, said solution being administered daily.

* * * * *